(12) United States Patent
Cima (10) Patent No.: US 10,967,122 B2
(45) Date of Patent: Apr. 6, 2021

(54) SUBCUTANEOUS DRUG DELIVERY DEVICE WITH MANUAL ACTIVATION AND DEACTIVATION OF DRUG RELEASE

(71) Applicant: Massachusetts Institute of Technology, Cambridge, MA (US)

(72) Inventor: Michael J. Cima, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 366 days.

(21) Appl. No.: 15/745,367

(22) PCT Filed: Aug. 5, 2016

(86) PCT No.: PCT/US2016/045774
§ 371 (c)(1),
(2) Date: Jan. 16, 2018

(87) PCT Pub. No.: WO2017/027376
PCT Pub. Date: Feb. 16, 2017

(65) Prior Publication Data
US 2019/0001053 A1 Jan. 3, 2019

Related U.S. Application Data

(60) Provisional application No. 62/202,380, filed on Aug. 7, 2015.

(51) Int. Cl.
*A61M 5/142* (2006.01)
*A61K 9/00* (2006.01)
*A61K 31/57* (2006.01)

(52) U.S. Cl.
CPC ......... *A61M 5/1428* (2013.01); *A61K 9/0002* (2013.01); *A61K 9/0024* (2013.01);
(Continued)

(58) Field of Classification Search
CPC .................. A61M 5/1428; A61M 5/14276
See application file for complete search history.

(56) References Cited

U.S. PATENT DOCUMENTS 4,148,871 A 4/1979 Pitt et al.
4,351,337 A 9/1982 Sidman
(Continued)

FOREIGN PATENT DOCUMENTS

WO 03024503 A2 3/2003

OTHER PUBLICATIONS

Au, Anthony K., "Microvalves and Micropumps for BioMEMS", Micromachines 2011, 2, 179-220; doi:10.3390/mi2020179. (pp. 42).
(Continued)

*Primary Examiner* — Nathan R Price
*Assistant Examiner* — Dung T Ulsh
(74) *Attorney, Agent, or Firm* — Eversheds Sutherland (US) LLP (57) ABSTRACT

Abstract of the Disclosure Implantable drug delivery devices and methods of making and using the same are provided. The implantable drug delivery devices permit selective activation and deactivation of drug delivery while subcutaneously implanted in a patient without the use of electronic equipment or power. The devices include a bistable member that has two stable states. In a first stable state, the bistable member does not close off a fluidic pathway between a drug reservoir and a drug release aperture, thereby allowing drug release from the device. In a second stable state, the bistable member closes off or narrows the fluidic pathway, thereby reducing or preventing drug release from the device. A patient or another person can reversibly change the bistable member between the first and second stable states by applying pressure on the patient's skin over the site of implanta-
(Continued)

tion and/or manipulating the device through the patient's skin at the site of implantation.

22 Claims, 6 Drawing Sheets

(52) U.S. Cl.
CPC ............ *A61K 9/0092* (2013.01); *A61K 31/57* (2013.01); *A61M 5/14276* (2013.01)

(56) References Cited

U.S. PATENT DOCUMENTS

| | | | |
|---|---|---|---|
| 4,450,150 A | 5/1984 | Sidman | |
| 4,548,607 A * | 10/1985 | Harris | A61M 5/1428 604/153 |
| 5,409,144 A * | 4/1995 | Brown | B65D 47/2031 220/203.17 |
| 5,468,501 A | 11/1995 | Kydonieus et al. | |
| 5,660,848 A | 8/1997 | Moo-Young | |
| 5,733,565 A | 3/1998 | Moo-Young et al. | |
| 5,853,406 A | 12/1998 | Masuda et al. | |
| 5,869,078 A * | 2/1999 | Baudino | A61K 9/0004 424/423 |
| 6,010,478 A * | 1/2000 | Bellhouse | A61M 5/3015 222/309 |
| 6,068,853 A | 5/2000 | Giannos et al. | |
| 6,186,982 B1 | 2/2001 | Gross et al. | |
| 6,296,621 B1 | 10/2001 | Masuda et al. | |
| 6,312,409 B1 | 11/2001 | Gross | |
| 6,508,808 B1 | 1/2003 | Carr et al. | |
| 6,565,526 B2 | 5/2003 | Seward | |
| 6,663,821 B2 | 12/2003 | Seward | |
| 7,637,889 B2 | 12/2009 | Glynn | |
| 7,776,024 B2 | 8/2010 | Santini, Jr. et al. | |
| 8,628,517 B2 | 1/2014 | Beebe et al. | |
| 8,707,792 B2 | 4/2014 | Shekalim | |
| 2002/0013555 A1* | 1/2002 | Seward | F16K 99/0036 604/247 |
| 2002/0090388 A1 | 7/2002 | Humes et al. | |
| 2004/0256584 A1* | 12/2004 | Zimmerling | F16K 31/086 251/7 |
| 2005/0131388 A1* | 6/2005 | Cheng | A61M 5/1428 604/891.1 |
| 2005/0192638 A1* | 9/2005 | Gelfand | A61N 1/3605 607/3 |
| 2006/0246103 A1 | 11/2006 | Ralph et al. | |
| 2007/0270932 A1* | 11/2007 | Headley | A61F 2/95 623/1.11 |
| 2008/0249510 A1 | 10/2008 | Mescher et al. | |
| 2009/0275925 A1* | 11/2009 | Langereis | A61K 9/0019 604/891.1 |
| 2011/0166522 A1* | 7/2011 | Haase | A61M 5/14276 604/151 |
| 2011/0301575 A1* | 12/2011 | Miesel | G01L 9/0072 604/891.1 |
| 2012/0090621 A1* | 4/2012 | van der Houwen | A61M 16/0468 128/207.16 |
| 2013/0005823 A1 | 1/2013 | Emigh et al. | |
| 2013/0053671 A1 | 2/2013 | Farra | |
| 2013/0218063 A1* | 8/2013 | Li | A61M 39/02 604/6.1 |
| 2013/0237922 A1* | 9/2013 | Davies | A61M 5/3294 604/205 |
| 2013/0324949 A1 | 12/2013 | Kliman | |
| 2014/0052063 A1* | 2/2014 | Gregory | A61M 16/209 604/99.03 |
| 2014/0107589 A1* | 4/2014 | Amirouche | A61M 5/16827 604/256 |
| 2014/0194851 A1 | 7/2014 | Burke et al. | |
| 2014/0296834 A1* | 10/2014 | Moss | A61K 9/0036 604/515 |

OTHER PUBLICATIONS

Balck, A., "Bistable Microvalve for Biomedical Usage", Design and Manufacturing of Active Microsystems, Microtechnology and MEMS, 2011 (pp. 375-392). (pp. 18).

Barth, J., "A Bistable Shape Memory Microswitch with High Energy Density", Smart Mater Struct., 19(2010) (pp. 9).

Goll, C., "Microvalves with Bistable Buckled Polymer Diaphragms", J. Micromech. Microeng. 6 (1996) 77-79. (pp. 4).

Gowrishetty, R. Usha, "Fabrication of Polyimide Bi-Stable Diaphragms Using Oxide Compressive Stresses for the Field of 'Buckle MEMS'", J. Micromech. Microeng. 20 (2010) (pp. 7).

Kota, S., "Design of Compliant Mechanisms: Applications to MEMS," Analog Integrated Circuits and Signal Processing, 29, 7-15 (2001). (pp. 9).

Ming, Y., "Experimental Study of Bistable Behaviors of Deployable Composite Structure", Journal of Reinforced Plastics and Composites OnlineFirst, Feb. 25, 2009. (pp. 11).

Santer, M., "Concept and Design of a Multistable Plate Structure", Journal of Mechanical Design, Aug. 2011, vol. 133. (pp. 7).

Qiu, J., "A Curved-Beam Bistable Mechanism", Journal of Microelectromechanical Systems, vol. 13, No. 2, Apr. 2004. (pp. 10).

Unverdi, U., "Design of a Compliant Bistable Lock Mechanism for a Dishwasher Using Functionally Binary Initially Curved Pinned-Pinned Segments", Thesis—Natural and Applied Sciences, Jun. 2012. (pp. 137).

Design Issues on Living Hinges—web.mit.edu/2.75/resources/random/Living%20Hinge%20Design. (pp. 9).

International Search Report and Written Opinion of the International Searching Authority for PCT/US2016/045774, dated Nov. 4, 2016. (pp. 11).

\* cited by examiner

SUBCUTANEOUS DRUG DELIVERY DEVICE WITH MANUAL ACTIVATION AND DEACTIVATION OF DRUG RELEASE

CROSS REFERENCE TO RELATED APPLICATIONS

This application claims priority benefit of U.S. Provisional Application No. 62/202,380, filed Aug. 7, 2015, which is incorporated by reference herein in its entirety.

BACKGROUND

The present disclosure generally pertains to implantable drug delivery systems and methods, including but not limited to devices and methods in which release of drug can be activated and deactivated while the device is implanted in a patient.

Implantable drug delivery devices are known. In some conventional designs, drug release is passive and continuous. For example, the drug may be combined with a polymeric matrix material which provides sustained release of the drug over an extended period. One example is the Nexplanon™ birth control implant. It is subcutaneously inserted and then releases progesterone for up to three years to prevent pregnancy.

Drug release cannot be turned off and on while the Nexplanon device remains implanted. Instead the device must be removed from the patient if the patient wishes to become pregnant, and a new device reinserted to resume birth control. The insertion and removal procedures are relatively simple for a physician but are not trivial. The devices are not designed for a patient to be able to activate or deactivate the drug release on her own. Because the device is not designed for a female patient to be able to activate and deactivate drug release on her own, the patient must seek the services of a physician to manage her birth control.

In other known implantable designs, drug release is actively controlled such that release of a drug can be provided in temporally spaced, discrete doses, on-demand or in accordance with a programmed schedule. An example of such an implantable device being developed by Microchips Biotech Inc. is described in U.S. Pat. No. 7,604,628 and U.S. Publication 2013/0053671 A1. These actively controlled devices, however, require power and electronics to operate. In addition, these microchip drug delivery devices have relatively complicated designs and may be difficult and expensive to manufacture relative to, for example, the Nexplanon device.

It therefore would be desirable to provide new and improved drug delivery devices that allow active control, including on-off functionality, of drug release. It would also be desirable to provide drug delivery devices that are operable without electric power and electronic controls—and their attendant costs and complexity. It furthermore would be desirable to provide a drug delivery device in which release of a drug can be manually turned on and off, preferably without any special tools or expertise, while the device remains implanted in a patient. Desirably, such a device would be capable of releasing therapeutic amounts of one or more drugs over an extended period such as from one to ten years, or in other cases longer or shorter periods.

SUMMARY

In one aspect, an implantable device for drug delivery is provided which includes a housing which comprises a drug reservoir; a drug formulation disposed in the drug reservoir, the drug formulation comprising a drug; at least one aperture extending through a wall of the housing through which the drug can diffuse to release the drug from the device; and a bistable member having a first stable state in which the member permits a fluidic pathway between the drug reservoir and the at least one aperture to be open to permit release of the drug by diffusion and a second stable state in which the member closes off the fluidic pathway to exclude release of the drug.

In another aspect, a method of administering a drug to a patient is provided which includes subcutaneously implanting an implantable drug delivery device including a bistable member at a site within a patient; positioning the bistable member of the subcutaneously implanted device in a first stable state; and permitting release of a drug from the device into the patient for a first treatment period.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

FIGS. 3A-3B are perspective views of part (including the bistable member) of the implantable drug delivery device shown in FIGS. 2A-2B, wherein FIG. 3A shows the bistable member in an open stable state and FIG. 3B shows the bistable member in a closed stable state in accordance with one example embodiment of the disclosure.

DETAILED DESCRIPTION

Drug delivery devices and methods are provided to address some or all of the aforementioned needs. In particular, an implantable drug delivery device has been designed that provides the capability to turn drug delivery on-off while implanted without electronic power or control. That is, the device advantageously is operable non-electrically (e.g., without the use of an electric pump, an electromagnetic actuator, a power source, or the like). In the present devices, drug release is typically driven by passive diffusion, and drug diffusion from the device can be manually activated or deactivated by the patient, for example, by pressing on the subcutaneously implanted device.

The device achieves this functionality by inclusion of a bistable member that has (i) a first stable state in which the bistable member does not close off a fluidic pathway between a drug reservoir and a drug release aperture (e.g. the fluidic pathway for drug release is open), thereby permitting release of drug from the device and (ii) a second stable state in which the bistable member closes off the fluidic pathway between the drug reservoir and the drug release aperture, thereby preventing, or at least substantially preventing, drug release from the device. The bistable member is elastically formable between the two stable states. The bistable member essentially operates as part of a reversible control valve. The device is configured for subcutaneous implantation at a site in a patient and shaped/dimensioned to permit the patient or another person to manually detect whether the bistable member of the subcutaneously implanted device is in the first or second stable state. The device is configured to permit the patient or another person to reversibly change the bistable member from the first stable state to the second stable state, and vice versa, by pressure on the patient's skin over the site of implantation and/or manipulation of the device through the patient's skin at the site of implantation.

The device may include one or more fiducial features to help prevent confusion. For example, the device may include fiducial markers (e.g., lettering, coloring, bumps, ridges, surface patterning, etc.) indicative of the orientation of the drug release aperture and/or the stable state of the bistable member. Such markers may be useful to the physician during implantation of the device in a patient.

In some embodiments, the rate of drug release can be tuned independently of the drug payload and method of loading by varying the architecture of the device. Thus, the device can be less dependent on the relative chemistries of the drug and device components for controlling drug release when compared to conventional formulation-based approaches for extended drug delivery.

In some embodiments, the drug delivery device includes drug stored at a high packing ratio and, therefore, alleviates the problem of having too large of a device volume considering that the device can be used over an extend period of time, which desirably may be for a period of years.

I. Implantable Drug Delivery Device

Figure 4:
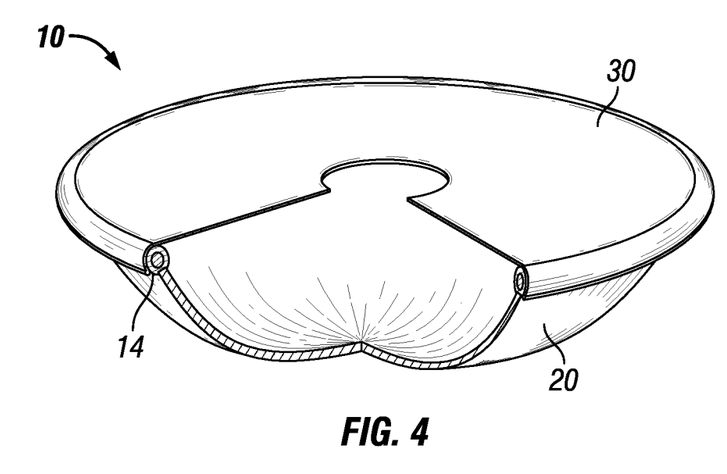
FIG. 4 is a perspective view with partial cut-away to show the interior of an implantable drug delivery device having a bistable member in accordance with one example embodiment of the disclosure.
Figure 5A:
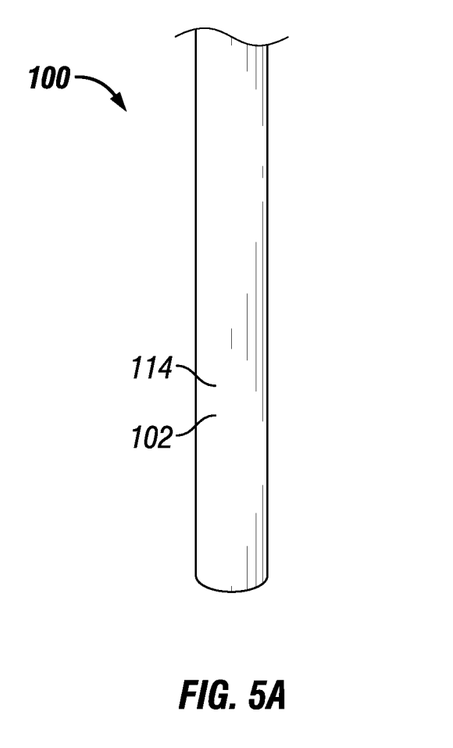
FIGS. 5A-5D show various illustrations of an implantable drug delivery device having a bistable member in accordance with another example embodiment of the disclosure.
Figure 5B:
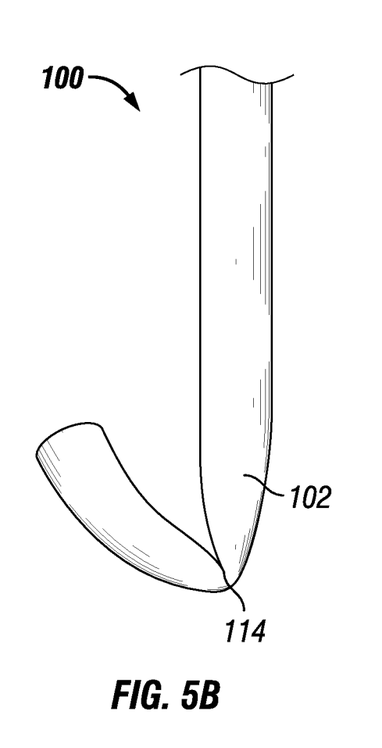
Figure 5C:
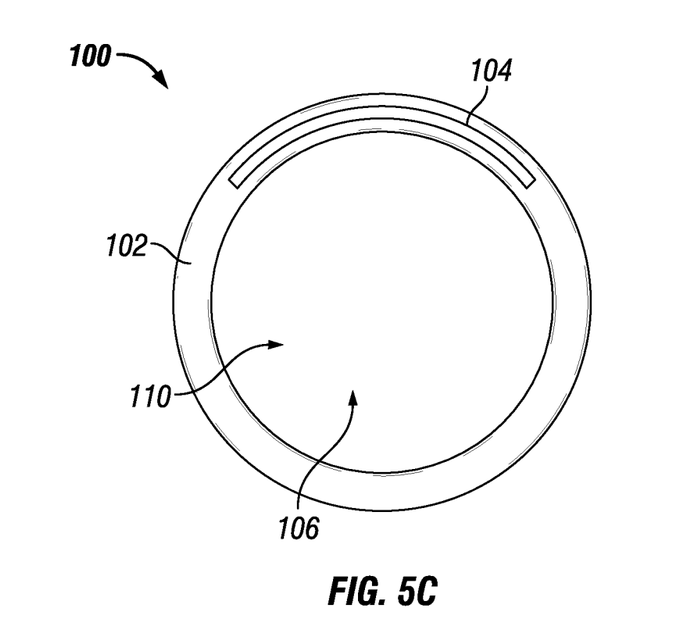
Figure 5D:
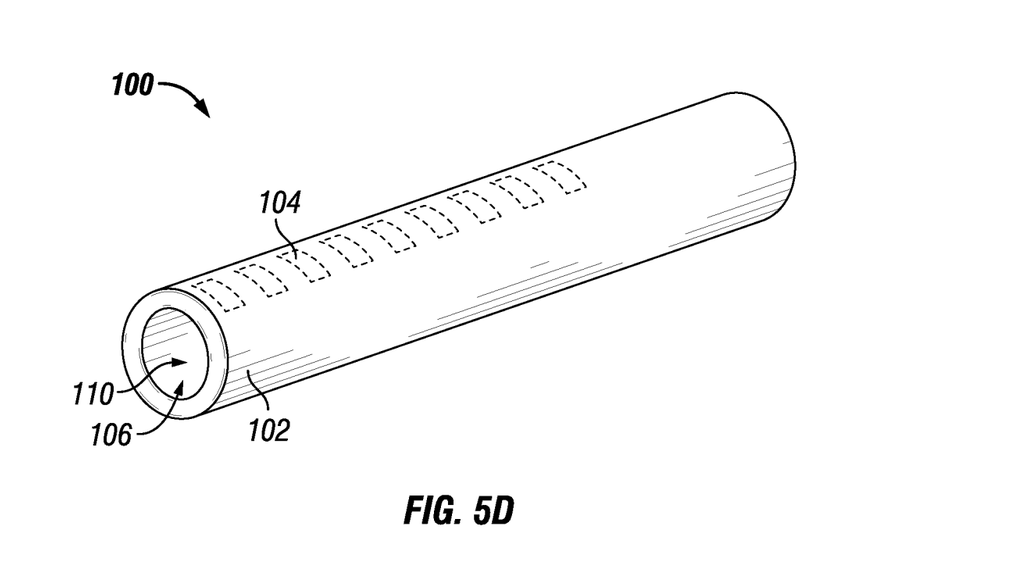
Figure 6:
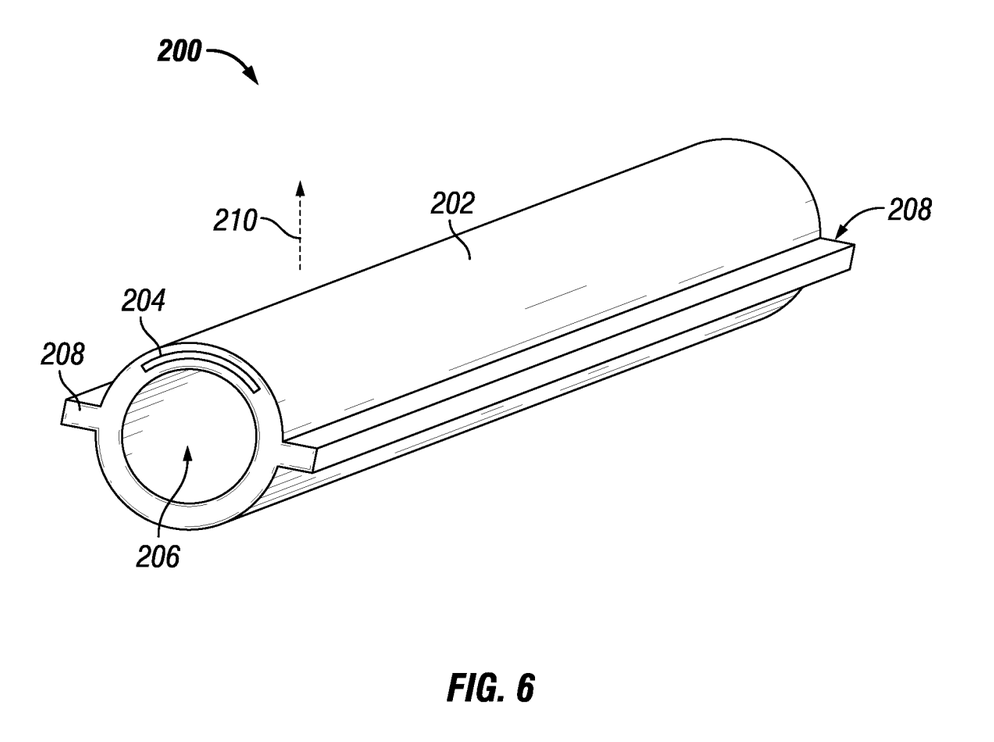
FIG. 6 is a perspective view of an implantable drug delivery device having a bistable member in accordance with yet another example embodiment of the disclosure.

Embodiments of drug delivery devices provided herein generally comprise a drug reservoir defined by/within a housing configured for subcutaneous drug delivery, as illustrated by the non-limiting embodiments shown in FIGS. 1-6. The drug delivery devices include a bistable member. In some embodiments, the bistable member is a bistable membrane. One embodiment of a device including a bistable membrane is illustrated in FIG. 1A to FIG. 4. The bistable member may also be in other forms, such as a ribbon operably associated with an elongate tube. Embodiments of such a device are illustrated in FIG. 5A to FIG. 6. The shape or form of the bistable member is not critical so long as the bistable member has the required or desired functionality described herein; specifically, the ability to turn on-off drug delivery from the device.

Figure 1A:
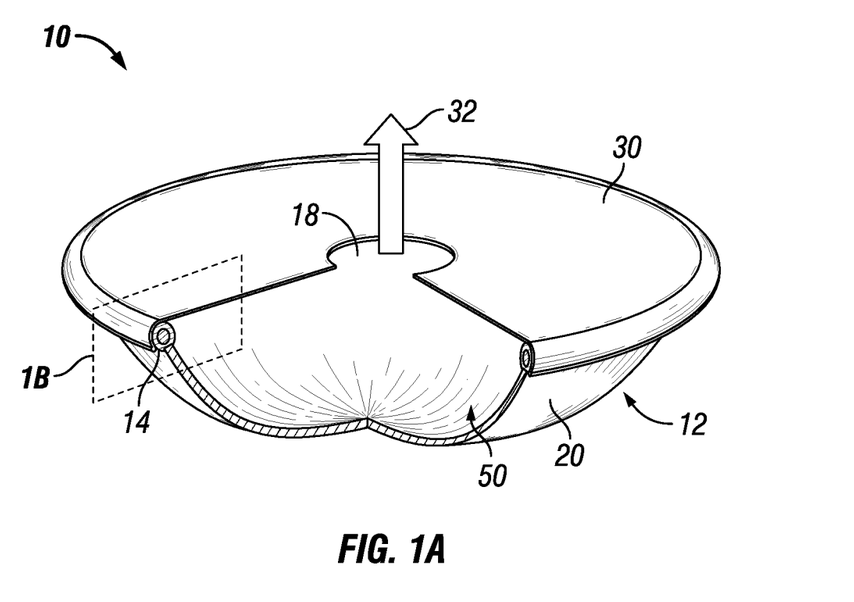
FIG. 1A is a perspective view with partial cut-away to show the interior of an implantable drug delivery device having a bistable member in accordance with one example embodiment of the disclosure.
Figure 1B:
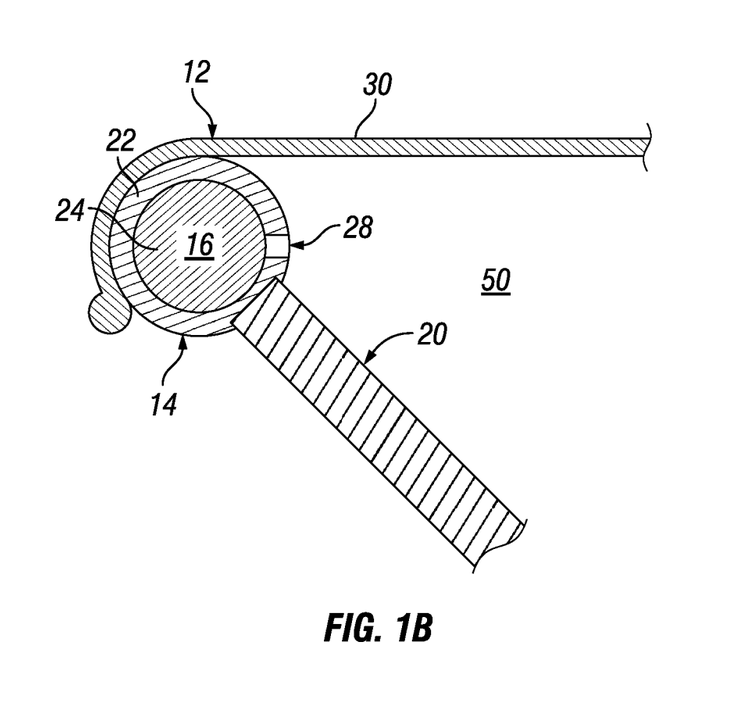
FIG. 1B is a cross-section view, taken along cut 1B, of part of the implantable drug delivery device shown in FIG. 1A.
Figure 2A:
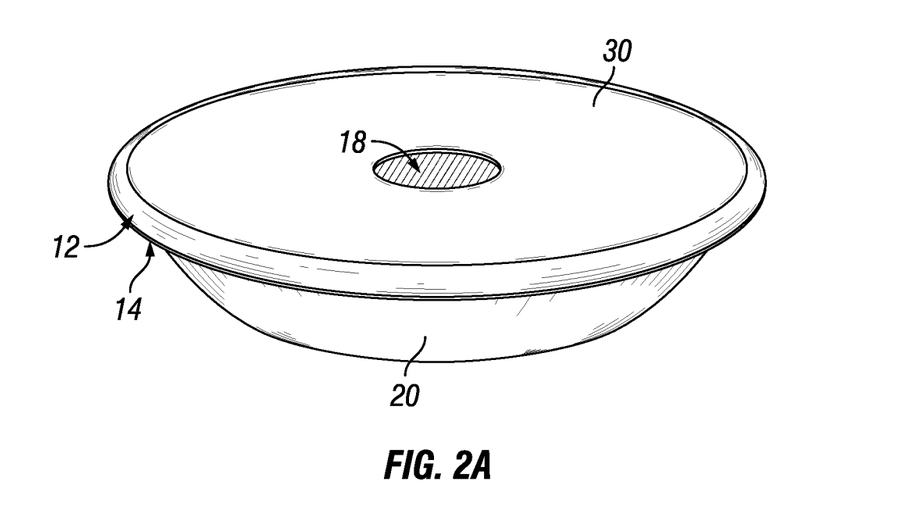
FIGS. 2A-2B are perspective views showing an implantable drug delivery device having a bistable member in an open stable state (FIG. 2A) and a closed stable state (FIG. 2B) in accordance with one example embodiment of the disclosure.
Figure 2B:
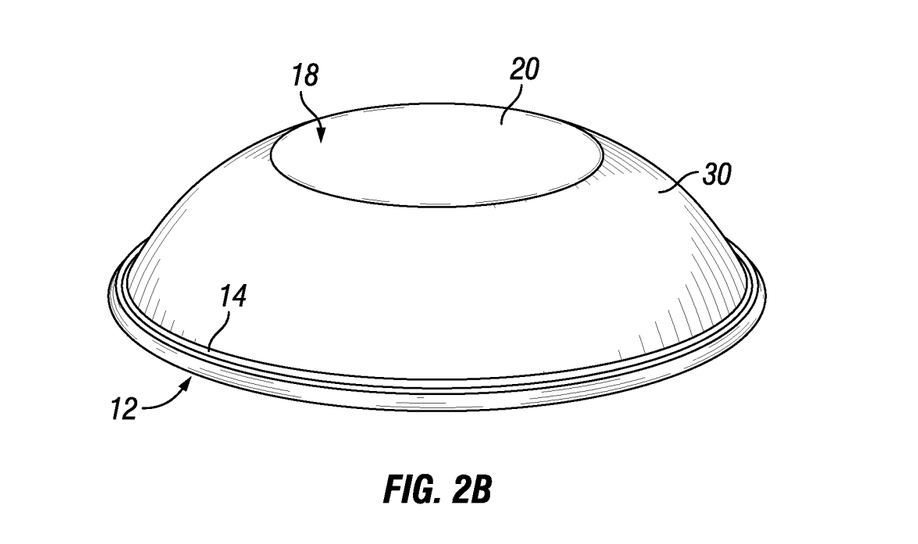
Figure 3A:
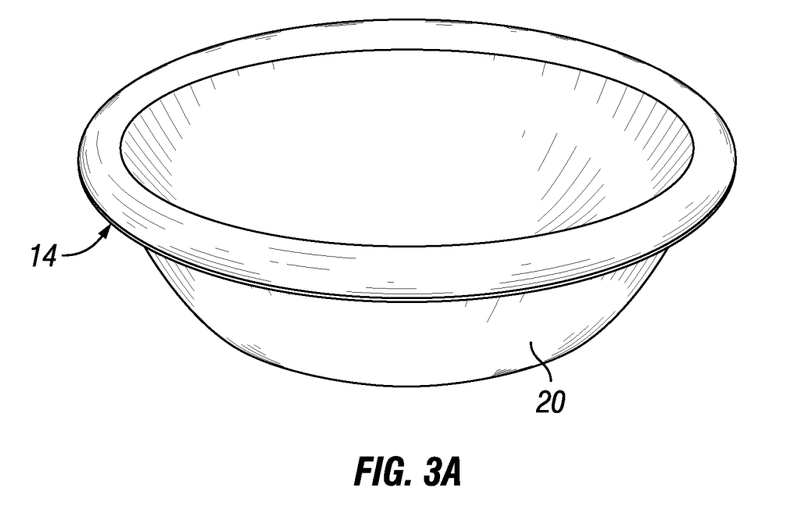
Figure 3B:
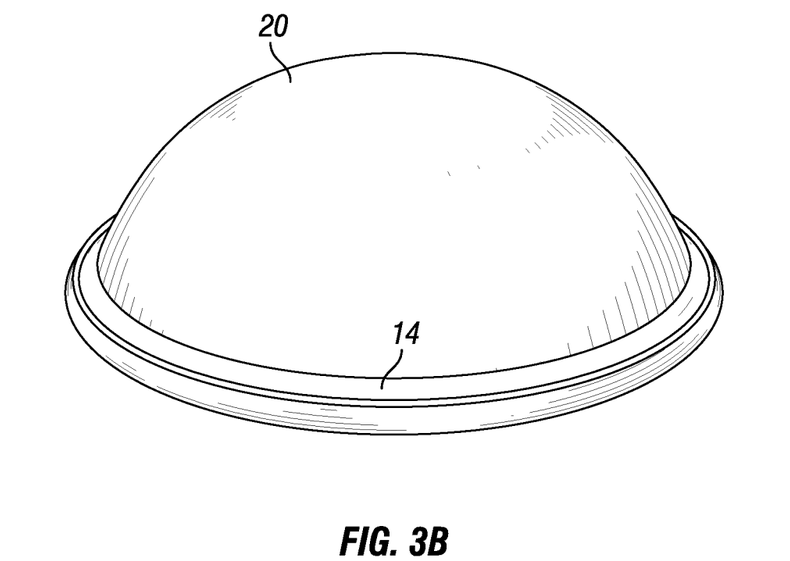

FIG. 1A shows the interior structure of one embodiment of a device in one of the stable states. FIG. 1B is a partial, cross-sectional view of the embodiment shown in FIG. 1A, taken along cut 1B. FIGS. 2A and 2B are perspective views of the embodiment illustrated in FIGS. 1A-1B, in the first and second stable states of the bistable membrane, showing the fluidic pathway for drug delivery open (FIG. 2A) and closed (FIG. 2B), respectively. FIGS. 3A and 3B are perspective views of the embodiment illustrated in FIGS. 1A-1B, in the first and second stable states of the bistable membrane, like FIGS. 2A-2B but with the sealing membrane omitted. FIG. 4 is an enhanced view of FIG. 1A.

FIGS. 1-4 show an implantable device 10 which includes a housing 12. The housing 12 includes a drug reservoir 14, a bistable membrane 20, and a sealing membrane 30. The drug reservoir 14 includes (i) an annular tube 22 in the form of a ring, wherein the annular tube defining and bounding a ring-shaped lumen 24, and (ii) a drug formulation 16 disposed in the ring-shaped lumen 24. In other embodiments, a drug reservoir lumen may be defined by a different shaped wall structure. The drug formulation 16 includes at least one drug, and optionally may include suitable excipients. The annular tube 22 supports and frames the sealing membrane 30, which extends across a first side of the ring. The sealing membrane 30 includes a wall that has at least one aperture 18 through which a drug can diffuse to release the drug from the device 10. Aperture 18 permits drug to diffuse out of implantable device 10 and into surrounding tissues, as shown by arrow 32. The aperture(s) may be centered within the ring, or the aperture(s) may be off-center. The annular tube 22 also supports and frames the bistable membrane 20, which extends across a second side of the ring, opposed to the first side. Device 10 has a space 50 defined between the sealing membrane 30 and the bistable membrane 20 in at least one stable state. The annular tube 22 includes at least one drug release perforation 28 which provides a fluid connection between the drug reservoir/lumen 24 and space 50.

Bistable membrane 20 has a first stable state that permits drug release from device 10. In the first stable state, which is illustrated in FIG. 1A, the at least one drug release perforation 28 and space 50 form a fluidic pathway between the lumen 24 of drug housing 14 and drug release aperture 18, thereby enabling drug release from device 10 via the fluidic pathway. Bistable membrane 20 also has a second stable state that prevents drug release from device 10. In the second stable state, bistable membrane 20 assumes a position that closes the fluidic pathway between the drug reservoir 14 and the drug release aperture 18. The device 10 can be manipulated to switch back and forth between the first and second stable states, opening and closing the fluidic pathway for drug release as needed.

Closing of the fluidic pathway with a bistable member can be accomplished with a number of different designs. For example, a bistable membrane can overlap and seal against a drug release aperture and/or against a drug release perforation to prevent diffusion of drug through the aperture and/or perforation. In an embodiment in which the drug release perforation 28 is sealed in the second (closed) stable state, drug is prevented from entering and accumulating in space 50, which can advantageously reduce or prevent an initial drug release burst when the bistable membrane 20 is switched back to the first stable state (the open state). This can prevent releasing a deleteriously high dose of drug when the bistable membrane 20 is switched back to the first stable state. In another example, the bistable membrane 20 can interface with the sealing membrane 30 to form a fluidic seal therebetween, thereby interrupting the fluidic pathway between space 50 and drug release aperture 18. By fluidically sealing space 50 off from drug release aperture 18, drug can diffuse out of drug housing 14 and accumulate in space 50. This can be advantageous, for example, when an initial drug release burst or a quicker initial drug release is desired. In yet another example, device 10 can be configured to close the fluidic pathway by simultaneously sealing the at least one drug release perforation 28 and forming a fluidic seal between bistable membrane 20 and sealing membrane 30. While the second stable state has been described as having space 50, those skilled in the art will appreciate that the second stable state need not have space 50 (e.g. there no is interior pocket for drug to accumulate in outside of drug housing 14).

The device 10 is configured for subcutaneous implantation at a site in a patient and is dimensioned to permit the patient or another person to manually detect whether the bistable membrane 20 of the device 10 is in the first or second stable state. The device is configured to permit the patient, or another person, to reversibly change the bistable membrane 20 from the first stable state to the second stable state, and vice versa, by pressure on the patient's skin over the site of implantation and/or by manipulation of the device through the patient's skin at the site of implantation.

A person of skill will readily appreciate that device 10 can assume any dimension and size suitable for subcutaneous implantation. In one non-limiting example, tube 22 of device 10 is a ring-shaped annular tube. In one embodiment, the ring has a diameter of about 1 cm, and the annular tube has a diameter of about 2 mm. In one embodiment, the annular tube may contain about 100 mg of a drug, and the device may be configured to deliver the drug, for example, at a rate of about 24 µg/day when the device is in the "on" state. In such a configuration, the device 10 may deliver the drug for about 11.3 years.

FIGS. 5A-5D show another embodiment of a drug delivery device 100, wherein the housing includes an annular tube 102, which at least in part defines a drug reservoir. Tube 102 has an elongate wall defining and bounding an elongate lumen 106, at least part of which serves as a reservoir for a drug payload. While tube 102 and lumen 106 are shown as an annular tube and cylindrical lumen respectively, tube 102 and lumen 106 may have other shapes provided that the shape permits effective operation of the bistable membrane associated therewith.

Tube 102 has a first end that includes a drug release aperture 110. Drug release aperture 110 can be coextensive in size with lumen 106, or it can be smaller than lumen 106. Tube 102 has a second end which is closed, or sealed. A drug formulation is disposed in the drug reservoir. The drug formulation includes a drug.

The region of lumen 106 between drug release aperture 110 and the drug payload forms a fluidic pathway for drug delivery. The fluidic pathway can include a valve section 114 that enables selective opening and closing of the pathway. When open, the fluidic pathway permits drug delivery from the drug reservoir to surrounding tissue via drug release aperture 110. When the fluidic pathway is closed, drug delivery from the drug reservoir to surrounding tissue via drug release aperture 110 is prevented.

Device 100 has a bistable member 104. Bistable member 104 can assume any suitable shape. In an exemplary embodiment shown in FIGS. 5A-5D, bistable member 104 has the form of a curved ribbon, which is fixed to or within tube 102 in a manner to transfer the bistability of the bistable member 104 to tube 102. Bistable curved ribbon structures are known in the art, e.g., metal measuring tapes.

Bistable member 104, and in turn tube 102, has a first stable state and a second stable state. In the first stable state, bistable member 104 is straight or unbent (as shown in FIG. 5A) such that lumen 106 and the fluidic pathway therein remains open to allow diffusion of drug from the drug reservoir, and out of the device and into a patient' body at the site of implantation, via drug release aperture 110 (e.g., valve section 114 is open). In the second stable state, bistable member 104 is bent to kink tube 102 (as shown FIG. 5B) and pinch closed lumen 106 and the fluidic pathway therein, such that diffusion of drug from the drug reservoir is blocked (e.g., valve section 114 is closed).

As shown in the cross-sectional view in FIG. 5C and in the partial perspective view in FIG. 5D, the annular tube 102 includes a bistable curved ribbon 104, which may extend part or all of the length of tube 102. In various embodiments, the bistable curved ribbon 104 may be coextruded with the annular tube 102, or it may be bonded to the outside or inside of the annular tube 102. In another embodiment, the curved ribbon 104 is formed separately and then inserted into a secondary channel lumen formed in a sidewall of the annular tube 102.

The lumen, or annulus, 106 of the tube 102 is loaded with a drug formulation, which may be in a solid or semi-solid form. In vivo, the drug dissolves and diffuses out of the drug release aperture 110 located at the first end of tube 102 when the bistable ribbon 104 is in the first stable state, as shown in FIGS. 5C-5D. The device 100 is configured to permit the patient, or another person, to reversibly change the bistable ribbon 104 from the first stable state to the second stable state, and vice versa, by pressure on the patient's skin over the site of implantation and/or by manipulation of the device through the patient's skin at the site of implantation.

FIG. 6 shows a perspective view of one variation of the device shown in FIGS. 5A-5D. Device 200 has a tube 202 which includes a bistable ribbon 204 and lumen 206. In FIG. 6, the bistable ribbon 204 and tube 202 are in the first stable state. Device 200 further includes a pair of tabs 208, which project from the outer sidewall of tube 202 and bias tube 202 bending in the kink direction 210, which is shown. In an alternative configuration (not shown), the tabs 208 project from an inner sidewall of the tube 202 into the lumen 206 and provide the same biasing functionality. In either configuration, the bistable member 204 is positioned between the tabs 208. Tabs 208 can be narrowed, tapered, or interrupted (e.g. no tabs) at a specific point or region of tube 202 to facilitate tube 202 bending at a specific point or region.

Housing/Construction

The device housing is constructed of biocompatible materials known in the art, in particular biocompatible polymeric materials. In embodiments, the housing may be made from one material or a combination of materials. The materials desirably are ones suitable for long term implantation into a patient.

The housing generally is made of a biocompatible polymeric material. In certain embodiments, the tube and/or the bistable member are formed from, or include, a biocompatible polymer selected from liquid crystal polymers, aromatic polyesters, polyamides, blends thereof, and combinations thereof. In certain embodiments, the sealing membrane is formed from, or includes, a biocompatible polymer selected from fluorosilicones, fluoroelastomers, chlorosulfonated polyethylenes, and combinations thereof.

In another embodiment, the bistable member is in the form of a thin curved ribbon, which may be made of a biocompatible metal. The ribbon is made to possess a "concavo-convex" cross-section, so that it has a transversely curved shape.

Fabrication of bistable members, such as membranes, is known in the art. The bistable member of the present devices may be formed from a single material or a combination of materials, such as a multilayer film or other composite structure. The bistable membrane or member may be joined to other parts of the device housing by any suitable securing means, including adhesives, mechanical fasteners, and the like.

In some embodiments, the housing defines multiple reservoirs, which may facilitate releasing two or more separate drug formulations from a single device, releasing drugs at two or more different release rates, or combinations thereof.

In one embodiment, the housing includes at least one radio-opaque portion or structure to facilitate in vivo detection or viewing of the device by a medical practitioner. In one embodiment, the housing is constructed of a material that includes a radio-opaque filler material, such as barium sulfate or another radio-opaque material known in the art. Fluoroscopy, X-ray, or other imaging techniques known in the art may be used.

In one embodiment, the housing further includes at least one suture loop, to aid in securing the implanted device and avoid or minimize device migration.

The housing may include a drug reservoir aperture or valve (e.g., a septum) or other orifice, so that a fluid can be injected into the reservoir. For example, it may be useful to inject a sterile saline into the device immediately prior to implantation of the device to "kick start" the drug dissolution process and reduce the lag time before drug release begins.

Drug Formulation

The drug formulation of the device includes at least one drug.

The drug can include essentially any therapeutic, prophylactic, or diagnostic agent that would be useful to deliver subcutaneously. In embodiments, it is an active pharmaceutical ingredient (API). As used herein, the term "drug" with reference to any specific drug described herein includes its alternative forms, such as salt forms, free acid forms, free base forms, and hydrates. In embodiments, the drug in the drug formulation may be a prodrug.

In one embodiment, the drug is a hormone. In a particular embodiment, the hormone is one useful in birth control, such as progesterone.

The drug formulation may include at least one excipient, preferably in a minor amount. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug. The excipient generally is not of a type or amount that would be characterized as a matrix material.

In various embodiments, the drug formulation may be in a solid form, semi-solid form (e.g., an emulsion, a suspension, a gel or a paste), or liquid form. In a preferred embodiment, the drug formulation is in a substantially solid form, such as in the form of a powder, granules, tablets, pellets, or a combination thereof, although other configurations are possible. The solid form advantageously may help reduce the overall volume of the drug payload in the device and thereby reduce the size of the device. A solid or semi-solid drug formulation generally becomes solubilized in the reservoir upon interstitial fluid entering the drug reservoir in vivo. The solubilized form of the drug then can be released by diffusion through one or more apertures in the device. As used herein, the term "solubilized form" includes pure solutions as well as suspensions of drug particles dispersed in a liquid carrier. Such suspensions may include microparticulate or nanoparticulate forms of the drug.

II. Applications and Use

Methods of treating a patient with a drug delivery device are provided. As used herein, the term "patient" may include a human or other mammal. The drug delivery device may be implanted in the patient to release drug for local, regional, or systemic administration of the drug.

In one embodiment, a method of administering a drug to a patient is provided which includes (i) subcutaneously implanting one of the drug delivery devices described herein at a site within a patient; (ii) positioning the bistable member of the subcutaneously implanted device in a first stable state (i.e. the aperture open state); and (iii) thereafter permitting release of the drug from the device into the patient for a first treatment period. In one embodiment, the method further includes, following the first treatment period, positioning the bistable member of the subcutaneously implanted device in the second stable state to stop release of the drug from the device into the patient for a first dormant period. This change in position of the bistable member from the first stable state to the second stable state may be performed manually by applying pressure on the patient's skin at the site of implantation and/or by manipulation of the device through the patient's skin at the site of implantation. The method may include manually detecting whether the bistable member of the implanted device is in the first or second stable state by assessing the presence or absence of a nodule under the skin of the patient at the site of implantation of the device. After the first dormant period, the method may include repositioning the bistable member of the implanted device in the first stable state to again permit release of the drug from the device into the patient for a second treatment period. This change in position of the bistable member from the second stable state to the first stable state also may be performed manually by applying pressure on the patient's skin at the site of implantation and/or by manipulation of the device through the patient's skin at the site of implantation. This on-off and off-on switching can be repeated as needed to deliver the drug over various periods of treatment and dormancy, as medically appropriate.

In a particular embodiment, the method is used in birth control. For example, a female patient may have the device implanted subcutaneously to release progesterone over a treatment period during which she wishes to avoid pregnancy. The device may be on at the time of implantation or switched on after implantation. At a later time, she may wish to become pregnant and can herself—without requiring a physician—switch off the implanted drug delivery device (stopping release of progesterone). At a later time, for example, after a pregnancy/birth, she could elect to switch the device back on (resuming release of progesterone). Such a device would be particularly desirable for a woman who lacks convenient and/or ready access to physicians, pharmacies, and the like, as in some developing countries.

Release of the drug from the device is generally driven by diffusion. In some embodiments, the release rate may be limited primarily or exclusively by diffusion of the drug through drug release perforations in the walls (e.g. tube) forming a drug reservoir. In other embodiments, the release rate may be limited by diffusion of the drug through a drug release aperture in a sealing membrane or at a first end of a tubular housing. The release rate may be tailored at least in part based on the size and number of drug release apertures, the size and number of drug release perforations, the surface area of the tube, the drug formulation, (e.g., its solubility), and the position of the drug release apertures relative to the position of any drug release perforations or drug itself.

The device may provide extended, continuous, intermittent, or periodic release of a selected quantity of a drug over a period that is therapeutically or prophylactically desirable. In one embodiment, the device can deliver the desired dose of drug over an extended period, such as 30, 60, 90, 120, or 180 days, or 1 to 12 years, e.g., 2, 3, 6, 8, 10, years, or more. The rate of delivery and dosage of the drug can be selected depending upon the drug being delivered and the disease or condition being treated. The release kinetics of the device can be tailored by varying the number and size of the apertures in the device, the number and size of the drug release perforations, or the composition of the drug formulation therein, among other device and drug parameters.

In embodiments, the drug delivery device is non-resorbable. In such embodiments, the device may be removed after a desired period following implantation. In one such a case, the method further includes removing the drug delivery device following release of the drug. In still other embodiments, the device may be removed even though a portion of the drug remains in the device.

III. Methods of Manufacture/Assembly

Methods of making an implantable drug delivery device are also provided. Generally, the method includes forming a drug formulation, forming a housing, and loading the drug formulation into a reservoir in the housing through an opening, and then closing off the opening.

In some embodiments, forming a drug formulation entails forming a drug formulation that includes one or more active pharmaceutical ingredients (APIs), and optionally combining it with one or more excipients. The method may include forming the drug formulation into a specified solid form suitable for filling a drug reservoir. Methods of forming solid drug formulations generally are known in the art, and include granulating the drug formulation to produce a high concentration drug formulation with specific physicochemical properties (e.g., solubility, dissolution rate, etc.). Optionally thereafter, the granulated or powdered drug formulation may be compacted, for example into mini- or micro-tablets. Desirably, the compacted solid drug formulation has dimensions and a shape that are substantially similar to that of the reservoir so that it may be easily contained in the reservoir. In other embodiments, the drug is formulated as a liquid or semi-solid which can be injected into the reservoir.

The tube and drug reservoir, and/or other parts of the housing, may be formed using a variety of methods known in the art, such as injection molding, compression molding, extrusion molding, transfer molding, insert molding, thermoforming, casting, or a combination thereof. In one particular embodiment, the housing is formed using precision injection molding. The housing is formed with a hollow interior, defining a reservoir for holding a drug formulation.

Forming a housing also may include forming one or more apertures through the housing. In particular embodiments, the aperture is formed through the housing and/or through a wall of the tissue interfacing member, such as by mechanically punching, mechanical drilling, or laser drilling one or more holes, or such as by injection molding, forming, or casting the housing or tubular body with a hole formed therein. Forming an aperture generally includes sizing and positioning the aperture to achieve a selected release rate for the drug formulation once the device is implanted. In embodiments, the step of forming the housing may also include forming multiple different drug reservoirs in a single housing, such as by integrating one or more partitioning structures in the housing.

Once the housing and drug formulation are produced, these components are combined using appropriate methods to yield the assembled device. In embodiments, the drug formulation is loaded through a fill opening in a wall of the housing and then the fill opening is sealed. In one embodiment, the loading step is done before, or after, the sealing membrane and the bistable membrane are combined with the annular tube defining the drug reservoir.

In other embodiments, the bistable member is integrally formed with the sealing member and/or other portions of the device housing.

In embodiments, the device is assembled using sterile techniques, for example, assembly in a clean room environment and sterilization using ethylene oxide gas, irradiation, or high intensity pulsed light. The sterilization technique will depend upon the sensitivity of the components used, such as the tendency for polymers and drugs to degrade after exposure to radiation. The device then may be vacuum-sealed in a polymeric package prior to distribution to reduce the amount of moisture or air that could potentially cause any one of the components to become contaminated or prematurely decompose during its shelf life.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

I claim:

1. An implantable device for drug delivery comprising:
   a housing which comprises a drug reservoir;
   a drug formulation disposed in the drug reservoir, the drug formulation comprising a drug;
   at least one aperture extending through a wall of the housing through which the drug can diffuse to release the drug from the device; and
   a bistable member having a first stable state in which the member permits a fluidic pathway between the drug reservoir and the at least one aperture to be open to permit release of the drug by diffusion and a second stable state in which the member closes off the fluidic pathway to exclude release of the drug,
   wherein the bistable member is manually reversibly and elastically formable between the first and second stable states.

2. The device of claim 1, wherein the device is configured for subcutaneous implantation at a site in a patient and is dimensioned to permit the patient or another person to manually detect whether the bistable member of the device, when subcutaneously implanted, is in the first or second stable state.

3. The device of claim 2, which is configured to permit the patient or another person to reversibly change the bistable member from the first stable state to the second stable state, and vice versa, by pressure on the patient's skin over the site of implantation and manipulation of the device through the patient's skin at the site of implantation.

4. The device of claim 1, wherein the bistable, member is a bistable membrane and the housing comprises an annular tube in the form of a ring, wherein the annular tube has a ring-shaped lumen therein, and the drug formulation is disposed in the ring-shaped lumen.

5. The device of claim 4, wherein the annular tube supports and frames:
   (i) a sealing membrane extending across a first side of the ring, the sealing membrane being the wall of the housing having the at least one aperture through which the drug can diffuse to release the drug from the device; and (ii) the bistable membrane extending across a second side of the ring, opposed to the first side.

6. The device of claim 5, wherein the annular tube includes at least one drug release perforation which provides a fluid connection between the drug reservoir and a space defined between the sealing membrane and the bistable membrane at least when the bistable membrane is in the first stable state.

7. The device of claim 6, wherein the bistable membrane in the second stable state further closes off the at least one drug release perforation.

8. The device of claim 5, wherein the sealing membrane comprises a biocompatible polymer selected from the group consisting of fluorosilicones, fluoroelastomers, chlorosulfonated polyethylenes, and combinations thereof.

9. The device of claim 1, wherein the bistable, member is in the form of a bistable curved ribbon.

10. The device of claim 9, wherein the housing comprises an annular tube and the bistable curved ribbon in the second stable state is bent to pinch closed the annulus of the tube.

11. The device of claim 10, wherein the bistable curved ribbon is fixed to or within the sidewall of the annular tube and extends in a direction parallel to the annulus of the annular tube.

12. The device of claim 11, further comprising a pair of elongated tabs for biasing the direction of bending of the annular tube.

13. The device of claim 1, wherein the drug formulation in the drug reservoir is in a solid or semi-solid form.

14. The device of claim 1, wherein the drug comprises a form of progesterone or another hormone.

15. The device of claim 1, wherein the bistable member comprises a biocompatible polymer selected from the group consisting of liquid crystal polymers, aromatic polyesters, polyamides, blends thereof, and combinations thereof.

16. The device of claim 1, wherein the device is operable 4 active and deactivate drug delivery without a pump and/or without electrical power.

17. A method of administering a drug to a patient comprising:
    subcutaneously implanting the device of claim 1 at a site within a patient;
    positioning the bistable member of the subcutaneously implanted device in the first stable state; and
    permitting release of the drug from the device into intra the patient for a first treatment period.

18. The method of claim 17, further comprising, following the first treatment period, positioning the bistable member of the subcutaneously implanted device in the second stable state to stop release of the drug from the device into the patient for a first dormant period.

19. The method of claim 18, further comprising, following the first dormant period, repositioning the bistable member of the subcutaneously implanted device in the first stable state to again permit release of the drug from the device into the patient for a second treatment period.

20. The method of claim 17, wherein the positioning, or the repositioning, of the bistable member is performed manually by pressure on the patient's skin at the site of implantation and/or manipulation of the device through the patient's skin at the site of implantation.

21. The method of claim 17, further comprising manually detecting whether the bistable member of the implanted device is in the first or second stable state, by assessing the presence or absence of a nodule under the skin of the patient at the site of implantation of the device.

22. The method of claim 17, wherein the drug comprises a form of progesterone or another hormone.

* * * * *